United States Patent
Yu et al.

(10) Patent No.: US 9,936,756 B1
(45) Date of Patent: Apr. 10, 2018

(54) CONCUSSION SENSING SYSTEM WITH CLOUD-BASED PREDICTION MODEL UPDATE

(71) Applicants: Aaliyah Yu, San Jose, CA (US); Maddox Yu, San Jose, CA (US)

(72) Inventors: Aaliyah Yu, San Jose, CA (US); Maddox Yu, San Jose, CA (US)

(73) Assignee: Aegis of Soteria LLC, San Jose, CA (US)

( * ) Notice: Subject to any disclaimer, the term of this patent is extended or adjusted under 35 U.S.C. 154(b) by 0 days.

(21) Appl. No.: 15/713,579

(22) Filed: Sep. 22, 2017

(51) Int. Cl.
*A61B 5/02* (2006.01)
*A42B 3/04* (2006.01)
*A61B 5/00* (2006.01)
*A63B 71/10* (2006.01)
*G06F 19/00* (2018.01)
*A42B 3/22* (2006.01)

(52) U.S. Cl.
CPC .............. *A42B 3/046* (2013.01); *A42B 3/222* (2013.01); *A61B 5/4528* (2013.01); *A61B 5/6803* (2013.01); *A63B 71/10* (2013.01); *G06F 19/3418* (2013.01); *A61B 5/4064* (2013.01); *A61B 2562/0219* (2013.01)

(58) Field of Classification Search
CPC .... A42B 3/222; G06F 19/3431; A61B 5/4528
See application file for complete search history.

(56) References Cited

U.S. PATENT DOCUMENTS

| | | | |
|---|---|---|---|
| 5,621,922 A | 4/1997 | Rush | |
| 9,024,770 B2 | 5/2015 | Reuben | |
| 9,451,915 B1 | 9/2016 | Wong | |
| 2011/0184319 A1 | 7/2011 | Mack | |
| 2013/0150684 A1* | 6/2013 | Cooner | A61B 5/1101 600/301 |
| 2015/0040685 A1 | 2/2015 | Nicholson | |
| 2015/0173669 A1* | 6/2015 | Simon | G06F 19/3431 600/595 |
| 2016/0128415 A1* | 5/2016 | Tubbs | A42B 3/205 2/424 |
| 2016/0213299 A1* | 7/2016 | Allen | A61B 5/4064 |

(Continued)

*Primary Examiner* — Tejash Patel

(57) ABSTRACT

A system to monitor hit impact force and to predict the likelihood of a concussion which includes a wearable device with an impact sensor and an application processor for prediction, a smartphone mobile application, a cloud-based data storage system, and an algorithm improvement system. The wearable device is mounted to the player's helmet or other locations where the impact force to the head is measured and a prediction algorithm is used to predict the potential risk of concussion. The wearable device wirelessly communicates with a smartphone, where data is viewed and associated information is managed. The impact force data and all related information are also automatically uploaded from the smartphone to a cloud-based database for storage. An algorithm improvement system will periodically analyze the data in order to build a better prediction model between impact force measured and the concussion diagnosed. Once a better prediction algorithm for such model is identified, such algorithm will be sent to the smartphone and hence downloaded to each athlete's wearable device automatically for a better prediction of concussion risk.

11 Claims, 5 Drawing Sheets

(56) References Cited

U.S. PATENT DOCUMENTS

2016/0292509 A1\* 10/2016 Kaps .................. G06K 9/00718
2016/0331319 A1   11/2016 Kozloski
2017/0318360 A1\* 11/2017 Tran .................... A42B 3/0433

\* cited by examiner

CONCUSSION SENSING SYSTEM WITH CLOUD-BASED PREDICTION MODEL UPDATE

BACKGROUND OF THE INVENTION

1. Field of the Invention

The present invention relates generally to system and method to assess the potential risk to brain damage by measuring impact force and predicting the potential risk of concussion.

2. Description of the Background Art

Concussion due to sports activities, especially in American football, becomes a larger and larger concern for athletes, coaches, and family members. Historically, athletes are checked by medical personnel on the sideline by examining whether athletes displayed any symptom such as dizziness and confusion. In order to improve player safety and identify potential head injuries as early as possible, various electronic devices have been proposed and manufactured recently in attempts to provide real-time alerts of potential risk for concussion. However, those systems fall short in various categories.

A typical type of such electronic devices is usually mounted on the athlete's helmet, measures the impact g-force, and displays such measurement either on the device or relays such information to other devices such as smartphones. However, it is up to the user to determine whether such impact force will lead to a concussion or not. Others attempted to improve the assessment capability by uploading the information into an online database and allow medical personals and other experts to make a decision at a later time. Such approach does not improve the real-time feedback to athletes. Accordingly, those electronic concussion assessment devices may have a negative effect by providing a false sense of security.

What is needed is a system that can measure real-time impact force and use a reliable model to predict the likelihood of a concussion. Such prediction model shall be tuned periodically, and shall be updated automatically to the sensing device in order to increase the accuracy. Furthermore, such prediction model shall be customized to each athlete according to his or her concussion history since the likelihood of subsequent concussions after a first concussion could increase by a factor of five (5), according to various medical studies.

SUMMARY

The inventive system is used to monitor hit impact force and to predict the likelihood of a concussion and includes a wearable device with an impact sensor and an application processor for prediction, a smartphone mobile application, a cloud-based data storage system, and an algorithm improvement system. The wearable device is mounted to the athlete's helmet or other locations where the impact force to the head can be measured. The prediction algorithm is run constantly inside the device based on the impact force measured from the sensor. If the algorithm predicts a potential risk for concussion, the device will alarm the player by sound and/or lights and/or on-screen display on the device. Such information will also be sent to smartphones that are wirelessly connected to such wearable device so that coaches and other personnel on the field can be alerted. Furthermore, with pre-approved permission, such information can be sent to family members, medical personnel and any other person of interest through the internet in real-time, so they will be alert to the athlete's situation.

The impact force data is also automatically uploaded from smartphone to a cloud-based database for easy access. With player's permission, further diagnosis by medical personnel will also be recorded into the same database. With enough data, periodic analysis can be conducted on such database in order to build better prediction models between impact force measured and the concussion diagnosed. Once a better prediction modeling algorithm is identified, such algorithm will be sent automatically to coaches' and athlete's smartphone and hence downloaded to each athlete's wearable device automatically.

Furthermore, such prediction model may take into consideration of each athlete's concussion history and impact force previously experienced, so that the model can predict the likelihood of subsequent concussion due to previous impact force this athlete experienced. When such prediction model is running on athlete's wearable device, it is customized to each athlete's unique impact force and concussion history.

The use of the same reference label in different drawings indicates the same or like components.

DETAILED DESCRIPTION

In the present disclosure, numerous specific details are provided, such as examples of apparatus, components, and methods, to provide a thorough understanding of embodiments of the invention. Persons of ordinary skill in the art will recognize, however, that the invention can be practiced without one or more of the specific details. In other instances, well-known details are not shown or described to avoid obscuring aspects of the invention.

Figure 1:
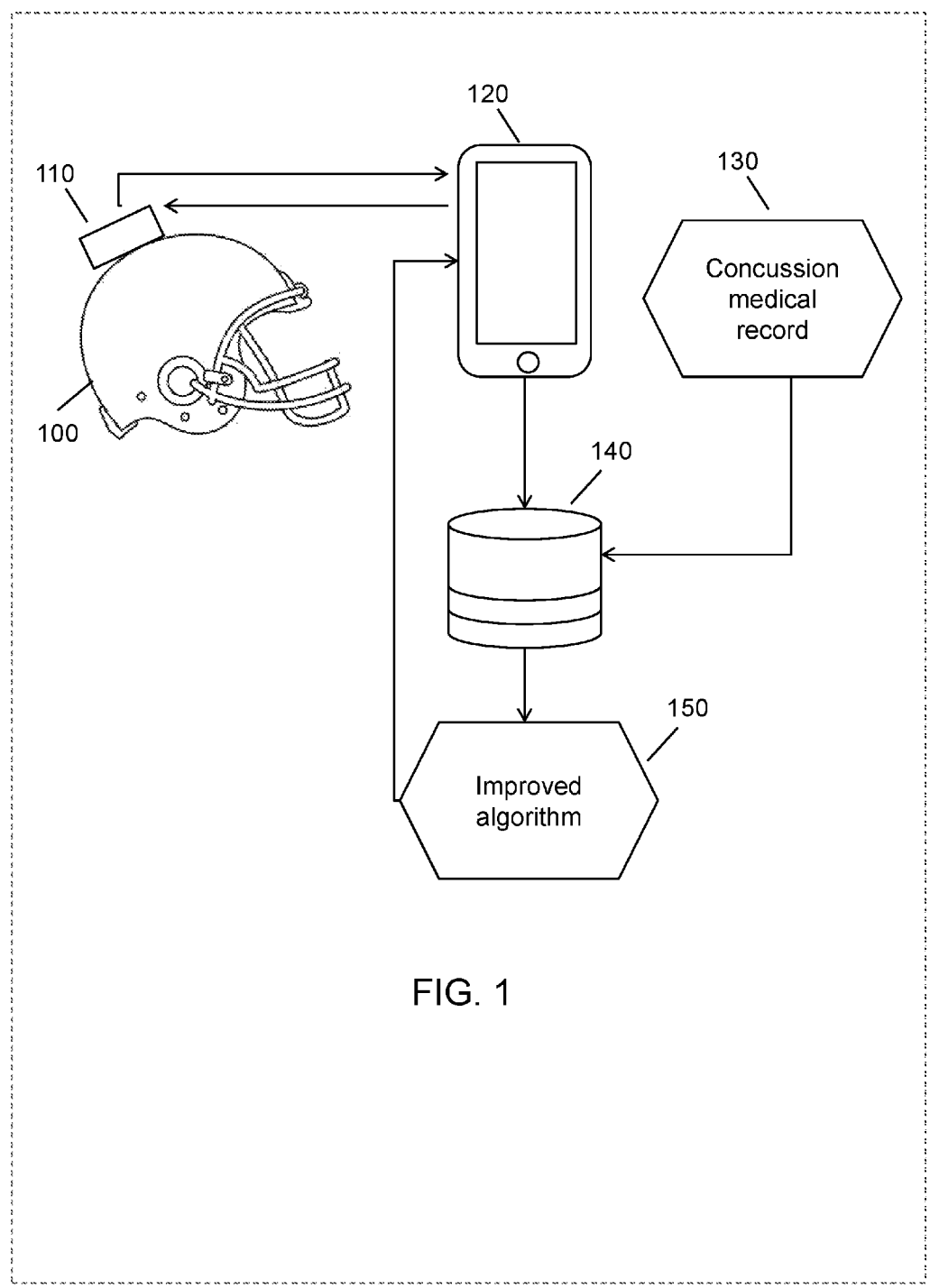
FIG. 1 is a schematic diagram of the system according to the present invention.
Figure 2:
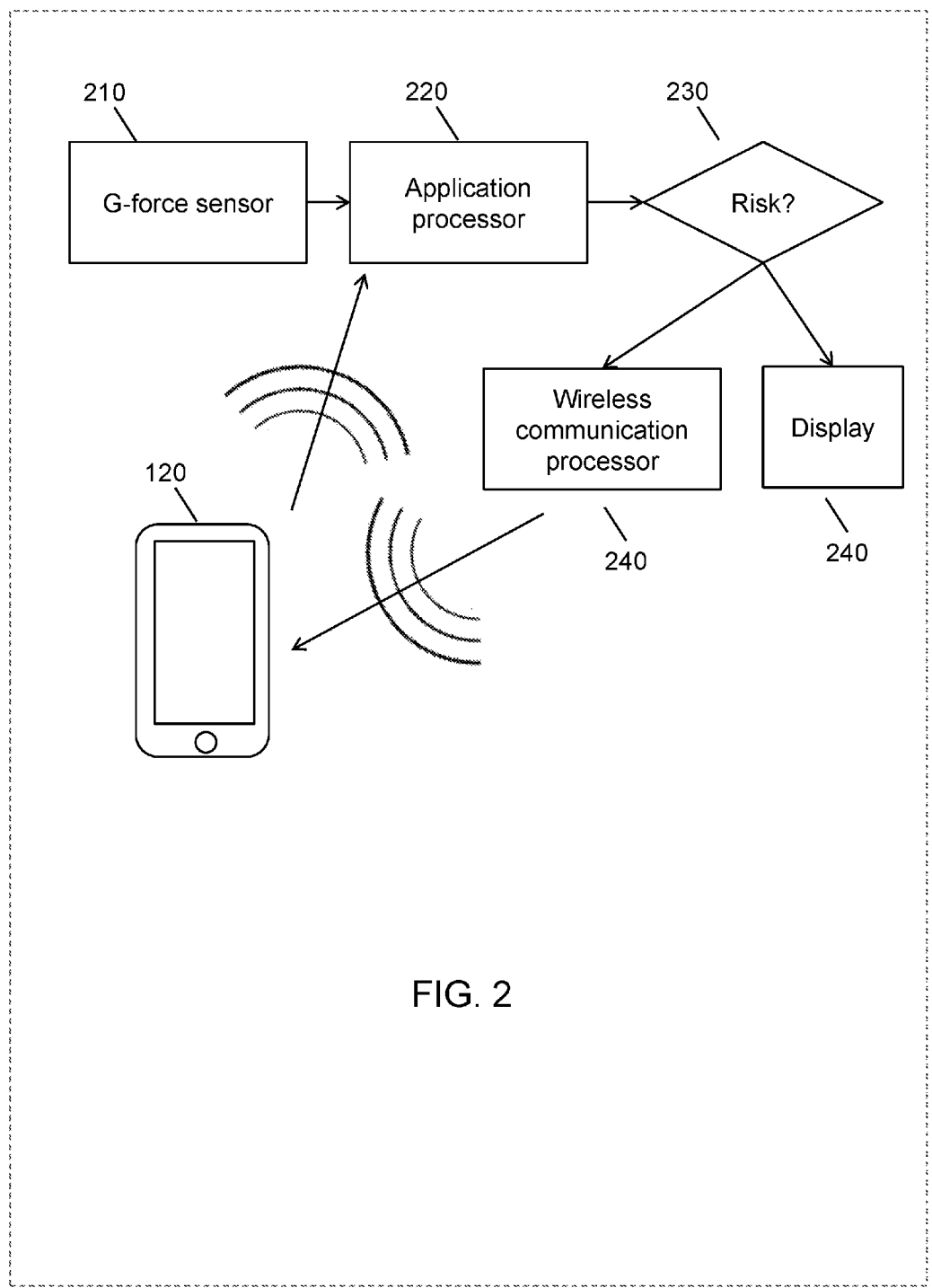
FIG. 2 schematically shows the major components of the wearable device and the information communication path between components of the wearable device and a smartphone.
Figure 5:
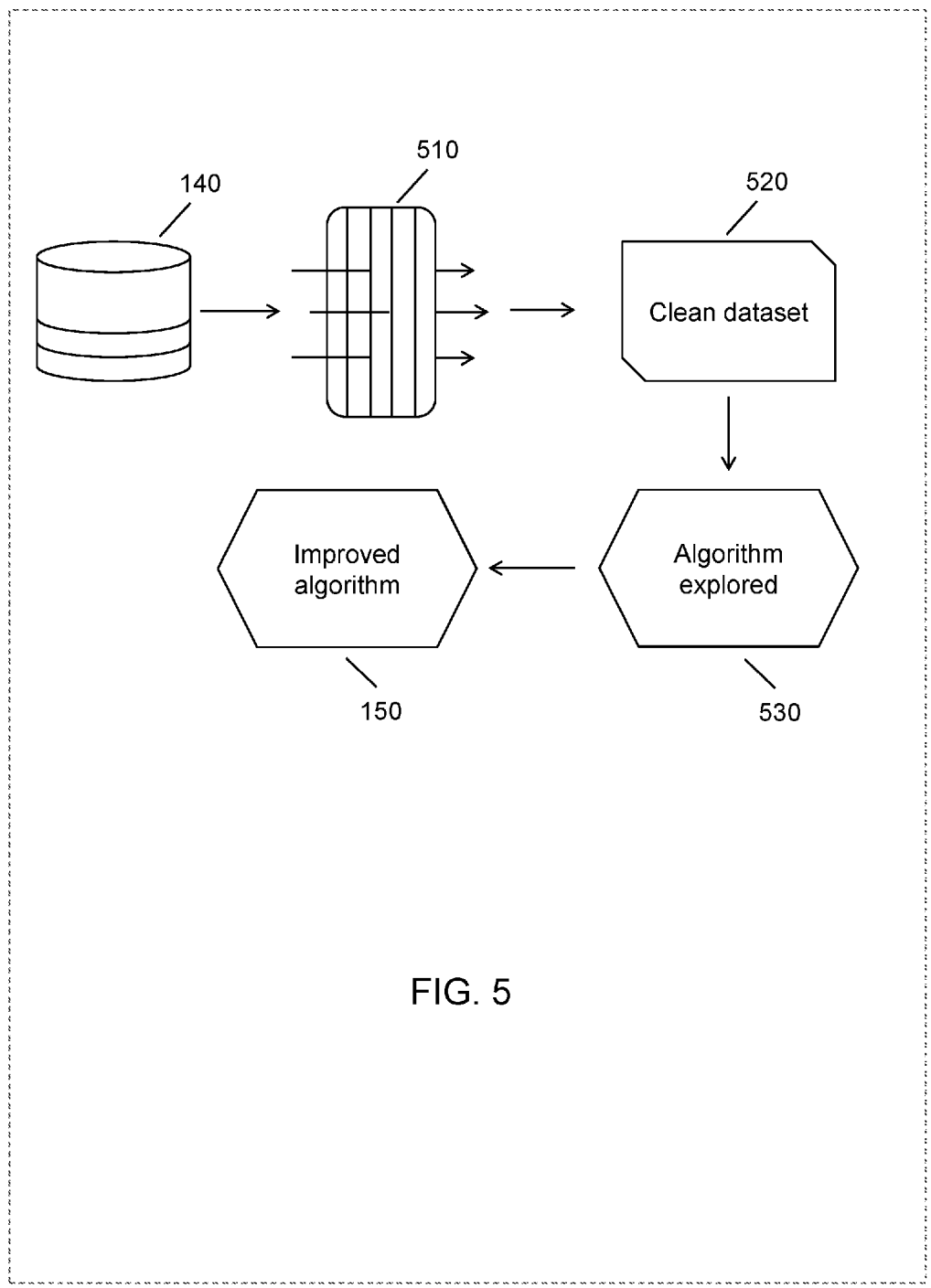
FIG. 5 is a flowchart of operations to improve the concussion risk prediction algorithm.

FIG. 1 shows a flow diagram schematically illustrating the operation of the system. The wearable device 110 is mounted to the player's helmet 100 or other locations where the impact force to the head can be measured. When the risk of concussion is detected (which is illustrated in FIG. 2 and will be further described below), the wearable device 110 sends the impact force measurement data, concussion risk prediction result, athlete's information (such as ID), and other related information to one or more smartphones 120 that is wireless connected to the wearable device 110 through Bluetooth or other wireless communication protocol. The smartphone 120 displays corresponding information and alert coaches, medical personnel, and/or other persons present, so that proper action can be taken to examine the athlete and potentially take necessary medical actions. The information is also uploaded through a wireless internet connection to a cloud-based storage system 140 (such as Amazon Web Service Cloud). If an athlete is diagnosed by medical personnel, with the athlete's permission, the corresponding medical record 130 can be uploaded into the same cloud-based storage system 140. With sufficient data volume, analysis can be performed on the data (which is illustrated in FIG. 5 and will be further described below) and a better algorithm 150 could be discovered to better predict the risk of concussion due to the impact force measured. Such improved algorithm 150 is then sent through the internet to the smartphone 120 and automatically downloaded to wearable device 110, in order to achieve better prediction. The algorithm 150 may also include parameters that are specific to an athlete's medical and impact force history, as stored in the cloud-based storage system 140, in order to achieve even more accuracy in prediction. Given that the wearable device 110 contains a unique ID that is specific to each player, it is possible to link the algorithm 150 for a specific wearable device 110 and hence to a specific athlete.

More detail about the wearable device is illustrated in FIG. 2. The wearable device comprises a g-force sensor 210 that may detect acceleration up to 400 g in three-dimensional space and may have measurement frequency up to milliseconds. The g-force measured is read by an application processor 220 which runs prediction algorithm to assess the potential risk of concussion. The algorithm can be as simple as whether the g-force measured exceeds certain pre-determined threshold, or can be based on industry standard such as the Gadd severity index from the US national highway traffic and safety administration (NHTSA) and the International Safety Organization (ISO), or can be based on unique algorithm developed (as illustrated in FIG. 5 and further explained below). If the potential risk is detected, as illustrated in operation 230, all related information will be sent from the wearable device to the smartphone, as described above, through the wireless communication process inside the wearable device. Furthermore, the wearable device may contain display component 240, such as a red LED warning light or a small size display, where it can provide a visual indication of the risk on such display components 240, such as a red flashlight or warning picture.

Figures 3A, 3B:
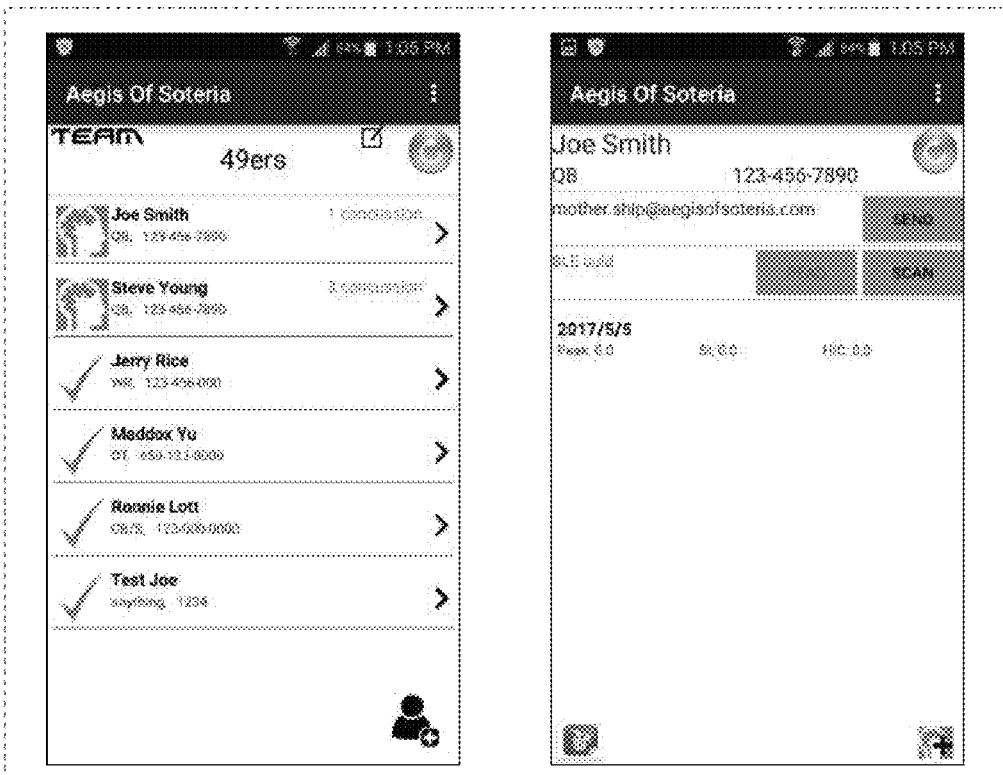
FIG. 3A-3B are the screenshots of the smartphone user interface of the present invention.

The connected smartphone 120 will receive related information and will displace on the screen. FIG. 3A and FIG. 3B are the screenshots of the smartphone user interface of the present invention. FIG. 3A shows the user interface where a group of athletes can be listed. High-level summary, such as whether each athlete has a history of concussion, could also be displayed here. When the user clicks on the name of a given athlete, the smartphone will display the user interface for the given player, as illustrated in FIG. 3B. Here, the user can view and manage the details of each player, communicate wirelessly with the athlete's wearable device, and/or send the athlete's information to other trusted parties. The user can also input the athlete's medical diagnosis result on this user interface, which will be uploaded to the same cloud-based storage. Many additional functions can be implemented in such smartphone application with reasonable effort.

Figure 4:
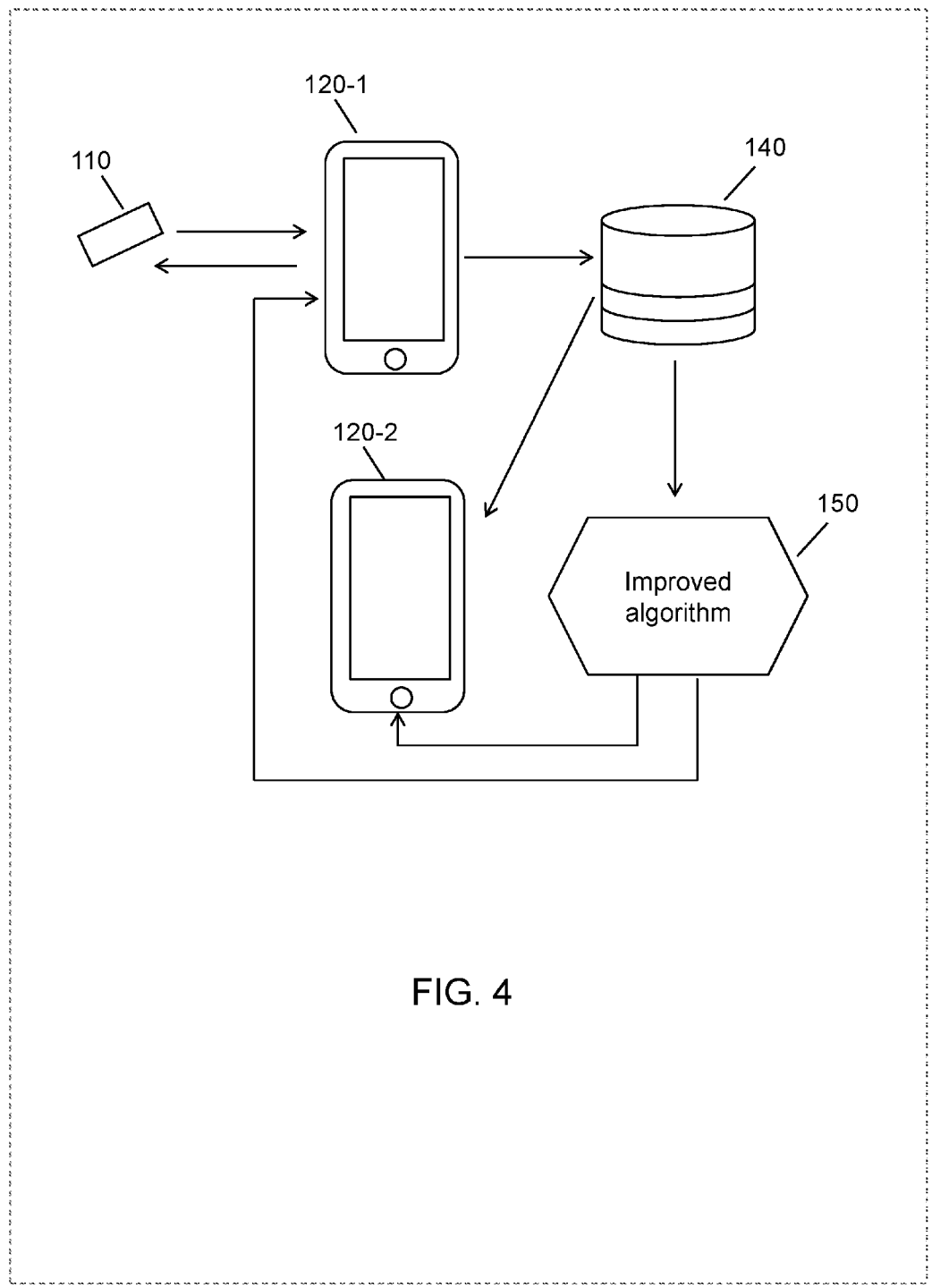
FIG. 4 is a flowchart of the information flow path between the smartphone and the cloud-based data storage system and algorithm improvement system.

Such related information is then sent to the cloud-based storage system 140, as illustrated in FIG. 4. In the example of FIG. 1, 120-1 is one instance of the smartphone, such as for the coach on the field. This smartphone 120-1 is wirelessly connected to an athlete's (or multiple athletes') wearable device(s) 110. When concussion-related information is received from a wearable device 110, the smartphone will automatically upload such information to the cloud-based storage system 140 using standard industry protocols and procedure. Such data stored will then enable further analysis to improve algorithm 150. If a trusted party, such as the family member of the athlete who wears the wearable device 110, is given permission to obtain such information, the cloud-based storage system 140 will automatically send that information to the smartphone 120-2 which belongs to this trusted party. This trusted part can only receive the information from the wearable device 110 which has a unique ID tied to this device. Alternatively, a user from smartphone 120-1 can manually trigger such information sharing to smartphone 120-2.

When sufficient data has been collected (usually at the range of hundreds of data points) in the cloud-based storage system 140, better prediction algorithm can be explored, as illustrated in FIG. 5. First, certain filtering operation 510 is done on the data stored so that only the data from athletes who have been given permission (for example, through smartphone app as illustrated in FIG. 3) is extracted for analysis. Also, data is further treated through the filtering operation 510 to remove any athlete's confidential information. This will generate a clean dataset 520. Then, a better algorithm can be explored, as illustrated by operation 530, through automatic machine learning algorithm as widely available at this moment or through manual analysis by data scientists or other experts. Once an improved algorithm 150 is identified, such algorithm will be sent automatically to each smartphone with the corresponding app, such as 120-1 and 120-2 in FIG. 4, and such algorithm will be automatically downloaded to wearable device 110 as illustrated in FIG. 1.

Note that, given the unique ID associated with each wearable device 110, it is possible to establish a unique relationship between the each athlete and his or her dataset. Hence, through machine learning or another method, the algorithm can have parameters that are specific for the given athlete. When the algorithm 150 is downloaded to the athlete's wearable device 110, only corresponding parameters for the unique ID of this wearable device is downloaded. When the application processor 220 inside the wearable device 110 predicts the risk for concussion, those parameters unique to this wearable device 110, and hence unique to this athlete, are used, in order to achieve better accuracy of prediction for this athlete. In one embodiment, an algorithm takes into consideration of the impact that is below the typical threshold of concussion risk. Even if such impact force individually is not strong enough to lead to an immediate concussion, if athlete experiences multiple such impacts in a short period of time, the algorithm would lower the threshold level where an impact would lead to concussion risk, based on this athlete's specific history.

While specific embodiments of the present invention have been provided, it is to be understood that these embodiments are for illustration purposes and not limiting. Many additional embodiments will be apparent to persons of ordinary skill in the art reading this disclosure.

What is claimed is:

1. A system for monitoring hit impact force and predicting the risk of concussion for an athlete, comprising:
   a wearable device operatively worn on the head of the athlete, which contains impact force measurement sensor to measure the g-force impact, an application processor to process the data and predict the risk of concussion, and a wireless communication processor to send information to a smartphone;

a smartphone mobile application that connect wirelessly to said wearable device, wherein the related information for the risk of concussion from the said wearable device is obtained wirelessly and displayed, wherein improved algorithm for prediction can be obtained from cloud-based system and sent to the connected wearable device, and wherein other data input and player administration function can be performed;

a cloud-based storage system, wherein the data and prediction from the said wearable device, any related information inputted from the said smartphone application potentially including athlete's medical record, and other data and information further inputted are stored; and an algorithm improvement system, wherein the data in the cloud-based storage system is used to develop a better algorithm to predict the risk of concussion, and such improve algorithm is delivered automatically or manually through the said smartphone application to the said wearable device.

2. The method of claim 1 further comprising:

additional administration and management functions in said mobile application to enable better management and communication of athlete's information;

potential additional procedure and method to input athlete's medical record into said cloud-based storage system; and potential method and function in said mobile application to share athlete's information and algorithm.

3. The system of claim 1, wherein said impact force measurement sensor in the said wearable device comprises an accelerometer that can measure high-g force at up to millisecond accuracy, a data-storage memory to store the measurement, and a battery.

4. The system of claim 1, where said application processor in said wearable device stores algorithm to predict potential risk of concussion based on the impact force measured by the said sensor as well as other information as need, including but not limited to athlete's historical record.

5. The system of claim 1, where said algorithm improvement system contains method where the improved algorithm is delivered, automatically or manually, to the said wearable device, with parameters that can be unique to each said wearable device, and used by said application processor to predict the risk of concussion.

6. A method for dynamically improving the prediction of risk of concussion by periodically update prediction algorithm on wearable devices, comprising:

a wearable device operatively worn on the head of the athlete, which contains impact force measurement sensor, an application processor to process the data and predict the risk of concussion with the prediction algorithm updated whenever a better version is available, and a wireless communication processor to send information to smartphone and receive improved prediction algorithm;

a smartphone mobile application that connect wirelessly to said wearable device, wherein the related information for concussion risk from said wearable device is obtained wirelessly and displayed, wherein improved algorithm for prediction can be obtained from cloud-based system and sent to the connected wearable device, and wherein other data input and player administration function can be performed;

a cloud-based storage system, wherein the data and prediction from said wearable device, any related information inputted from the said smartphone application potentially including athlete's medical record, and other data and information further inputted are stored, wherein all or part of the information is used for further improvement of the prediction algorithm; and an algorithm improvement system, wherein the data in the cloud-based storage system is used to develop a better algorithm to predict risk of concussion, and such improve algorithm is delivered automatically or manually through said smartphone application to said wearable device.

7. The method of claim 6, wherein said application processor in wearable device consists storage memory where the prediction algorithm is stored and updated when necessary.

8. The method of claim 6, wherein the said algorithm can be updated automatically by the algorithm improvement system to the smartphone application or can be updated manually when the user triggers demand on the wearable device and/or on the smartphone application to search for the latest version of the said prediction algorithm.

9. A method for improving the prediction of risk of concussion for the individual athlete by associating individual athlete's historical data with prediction algorithm and by using prediction algorithm specific optimized for the given individual, comprising:

a wearable device operatively worn on the head of the athlete, which contains impact force measurement sensor, an application processor to process the data and predict risk of concussion, and a wireless communication processor to send and receive information to smartphone including a unique electronic ID associated with the sensor and/or application process and/or wireless communication processor;

a smartphone mobile application that connect wirelessly to said wearable device, wherein the related information for concussion risk from said wearable device is obtained wirelessly and displayed, wherein improved algorithm for prediction can be obtained from cloud-based system and sent to the connected wearable device, and wherein other data input and player administration function can be performed including identification and association of the unique electric ID from said wearable device to the athlete who wears such wearable device;

a cloud-based storage system, wherein the data and prediction from said wearable device, any related information inputted from the said smartphone application potentially including athlete's medical record, and other data and information further inputted are stored, wherein all or part of the information is linked to the unique electric ID from said wearable device and the athlete who wear such wearable device; and an algorithm improvement system, wherein the data in the cloud-based storage system is used to develop better algorithm to predict risk of concussion, and such improved algorithm is delivered automatically or manually through said smartphone application to said wearable device.

10. The method of claim 9, wherein the improvement of the prediction algorithm takes into consideration of individual athlete's historical record stored in the said cloud-based storage system, including but not limited to the historical force of impact measured and historical concussion record, and attempts better prediction algorithm with parameters specific for a given athlete.

11. The method of claim 9, where the said improved algorithm is delivered to the wearable devices with parameters that are calculated based on individual athlete's historical data associated with the unique electric ID assigned for the unique wearable device for the athlete, wherein such parameters can be updated periodically when more data from the given athlete becomes available.

\* \* \* \* \*